(12) United States Patent
Asako

(10) Patent No.: US 7,524,666 B2
(45) Date of Patent: Apr. 28, 2009

(54) REDUCTASE GENE AND USE THEREOF

(75) Inventor: Hiroyuki Asako, Toyonaka (JP)

(73) Assignee: Sumitomo Chemical Company Limited, Tokyo (JP)

( * ) Notice: Subject to any disclaimer, the term of this patent is extended or adjusted under 35 U.S.C. 154(b) by 0 days.

(21) Appl. No.: 11/516,374

(22) Filed: Sep. 6, 2006

(65) Prior Publication Data
US 2007/0072278 A1    Mar. 29, 2007

(30) Foreign Application Priority Data
Sep. 9, 2005    (JP)    ............................. 2005-261862

(51) Int. Cl.
| | |
|---|---|
| C12N 9/02 | (2006.01) |
| C12N 1/20 | (2006.01) |
| C12N 15/00 | (2006.01) |
| C12P 7/00 | (2006.01) |
| C12P 21/04 | (2006.01) |
| C07H 21/04 | (2006.01) |
| C12Q 1/68 | (2006.01) |
| C12Q 1/00 | (2006.01) |
| C12Q 1/26 | (2006.01) |

(52) U.S. Cl. .............................. 435/189; 435/4; 435/6; 435/69.1; 435/71.1; 435/132; 435/252.3; 435/320.1; 435/440; 435/25; 536/23.2

(58) Field of Classification Search ........................ None
See application file for complete search history.

(56) References Cited

U.S. PATENT DOCUMENTS

2003/0186400 A1* 10/2003 Asako et al. ................. 435/146

FOREIGN PATENT DOCUMENTS

| JP | 10-000097 A | 1/1998 |
|---|---|---|
| JP | 2774341 B | 7/1998 |
| WO | 8907648 | 2/1989 |
| WO | 99/50223 A2 | 10/1999 |

OTHER PUBLICATIONS

Branden et al. Introduction to Protein Structure, Garland Publishing Inc., New York, p. 247, 1991.*
Yi-Fong Wang et al.; Lipase-Catalyzed Irreversible Transesterification Using Enol Esters: Resolution of Cyanohydrins and Syntheses of Ethyl (R)-2-Hydroxy-4-Phenylbutyrate and (S)-Propranolol; Tetrahedron letters, vol. 30, No. 15, pp. 1917-1920, Great Britain, (1989).
European Search Report for the corresponding European Patent Application No. 06254610; Feb. 2, 2007; 3 pages.
I. Kaluzna et al., "Enantioselective reductions of ethyl 2-oxo-4-phenylbutyrate by Saccharomyces cerevisiae dehydrogenases," J. Molecular Catalysis B: Enzymatic, 17:101-105 (2002).
I. Kaluzna et al., "Systematic Investigation of Saccharomyces cerevisiae Enzymes Catalyzing Carbonyl Reductions," J. Am. Chem. Soc., 126:12827-12832 (2004).
A. Chadha et al., "Asymmetric Reduction of 2-Oxo-4-Phenylbutanoic Acid Ethyl Ester By Daucus carota Cell Cultures," Tetrahedron: Asymmetry, 7, No. 6, 1571-1572 (1996).
D.H. Dao et al., "Stereochemical control in microbial reduction. Part 31: Reduction of alkyl 2-oxo-4-arylbutyrates by baker's yeast under selected reaction conditions," Tetrahedron: Asymmetry 9, 2725-2737 (1998).

* cited by examiner

*Primary Examiner*—Yong D Pak
(74) *Attorney, Agent, or Firm*—Panitch Schwarze Belisario & Nadel LLP

(57) ABSTRACT

Provided are genes coding a protein having an ability of asymmetrically reducing a 2-oxo-4-phenylbutyrate to produce a (R)-2-hydroxy-4-phenylbutyrate advantageously from the industrial standpoint, the protein, and methods of producing a (R)-2-hydroxy-4-phenylbutyrate using them. Genes having a base sequence coding an amino acid sequence shown in SEQ ID NO:1, or a base sequence shown by a base sequence shown in SEQ ID NO:2.

33 Claims, No Drawings

SEQUENCE LISTING

<160> NUMBER OF SEQ ID NOS: 17

<210> SEQ ID NO 1
<211> LENGTH: 304
<212> TYPE: PRT
<213> ORGANISM: Yamadazyma farinosa

<400> SEQUENCE: 1

Met Ser Phe Lys Lys Asp His Phe Thr Leu Ser Asp Asn Thr Thr Ile
1               5                   10                  15

Pro Ala Ile Gly Tyr Gly Leu Gly Thr Lys Trp Tyr Lys Gln Gly Val
            20                  25                  30

Asp Lys Ile Asp Glu Asn Val Val Phe His Leu Lys Gln Ala Ile Asp
        35                  40                  45

Ala Gly Leu Thr His Ile Asp Gly Ala Glu Val Tyr Asn Thr Asn Arg
    50                  55                  60

Glu Cys Gly Leu Ala Leu Lys Lys Val Asp Val Pro Arg Glu Lys Leu
65                  70                  75                  80

Tyr Ile Thr Asn Lys Phe Ile Pro Lys Asn Thr Lys Asp Asp Ser Ser
                85                  90                  95

Ser Pro Leu Lys Asp Pro Tyr Asp Ala Leu Lys Glu Asp Leu Lys Gln
            100                 105                 110

Phe Gly Val Asp Tyr Val Asn Leu Tyr Leu Ile His Cys Pro Phe Ile
        115                 120                 125

Glu Lys Glu Arg Asn Gly Tyr Thr Leu Val Glu Ala Trp Asn Arg Leu
130                 135                 140

Glu Lys Ala Leu Asp Asp Gly Leu Thr Lys Ser Ile Gly Val Ser Asn
145                 150                 155                 160

Phe Arg Val Glu Asp Ile Glu Glu Ile Leu Gln Ser Lys Pro Lys Tyr
                165                 170                 175

Thr Pro Val Val Asn Gln Ile Glu Phe Asn Ala Tyr Leu Gln Asn Gln
            180                 185                 190

Thr Pro Gly Ile Val Asp Tyr Cys Lys Lys His Asn Ile Leu Val Glu
        195                 200                 205

Ala Tyr Ser Pro Leu Gly Pro Val Thr Lys Gly Arg Pro Gly Pro Leu
    210                 215                 220

Asp Asp Thr Leu Val Glu Leu Ser Lys Lys Tyr Asn Lys Thr Glu Ser
225                 230                 235                 240

Gln Ile Leu Leu Arg Trp Val Leu Gln Gln Gly Ile Leu Pro Ile Thr
                245                 250                 255

Thr Ser Ser Asn Lys Glu Arg Leu Val Gln Ser Leu Glu Ile Phe Asn
            260                 265                 270

Phe Asp Leu Ser Lys Glu Asp Val Asp Thr Ile Ser Arg Leu Gly Thr
        275                 280                 285

Gln Lys His Leu Arg Gln Tyr Trp Thr Asn Glu Tyr Ser Lys Tyr Asp
    290                 295                 300

<210> SEQ ID NO 2
<211> LENGTH: 915
<212> TYPE: DNA
<213> ORGANISM: Yamadazyma farinosa
<220> FEATURE:
<221> NAME/KEY: CDS
<222> LOCATION: (1)..(915)

<400> SEQUENCE: 2

```
atgtcgttca aaaaggatca cttcacgctt tcggataaca ctacaattcc ggccataggt    60
tacggacttg gaaccaaatg gtataagcaa ggggtggata agatagacga aaatgtggtg   120
ttccacctca agcaagcaat tgacgcaggt ttgacacaca tagatggcgc agaagtatac   180
aacactaata gggaatgcgg cttggcactc aaaaaggtgg atgttcctcg tgaaaaactt   240
tacattacaa acaagtttat accaaaaaat actaaggacg actcgagctc tcccttaaaa   300
gatccatacg atgcattgaa ggaggatctc aaacagttcg gggttgacta tgtgaattta   360
tacttgatac attgcccttt cattgaaaag gagaggaacg gatacacttt ggtggaggct   420
tggaaccgtt tggagaaggc gttggatgat ggcttaacca aaagcattgg agtgtcgaat   480
ttccgtgtgg aggatattga ggaaattttg caatcaaagc ctaagtatac gccggttgtg   540
aaccagattg aattcaatgc gtacttgcag aaccagaccc caggaattgt tgattattgc   600
aaaaagcata acatcttggt cgaggcttac tctcccttgg gtcccgtaac taaaggcaga   660
ccgggtcctt tggatgacac tttggtcgag ttatcgaaga agtataacaa gacagagtct   720
cagattcttc ttagatgggt acttcagcaa ggtattttac ccatcacgac ttcttcgaac   780
aaggaacgtc tcgtgcaaag tctcgaaatt ttcaatttcg acctttctaa ggaagacgtg   840
gatactatct ccaggcttgg tactcaaaag catttgagac agtattggac caatgagtac   900
tcgaagtacg attaa                                                    915

<210> SEQ ID NO 3
<211> LENGTH: 12
<212> TYPE: PRT
<213> ORGANISM: Yamadazyma farinosa

<400> SEQUENCE: 3

Leu Val Gln Ser Leu Glu Ile Phe Asn Phe Asp Leu
1               5                   10

<210> SEQ ID NO 4
<211> LENGTH: 19
<212> TYPE: DNA
<213> ORGANISM: Artificial Sequence
<220> FEATURE:
<223> OTHER INFORMATION: Designed oligonucleotide primer for PCR;
      r stands for g or a

<400> SEQUENCE: 4
rrtcraartt gaaaatttc                                                 19

<210> SEQ ID NO 5
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 5
aattaaccct cactaaaggg                                                20

<210> SEQ ID NO 6
<211> LENGTH: 930
<212> TYPE: DNA
<213> ORGANISM: Yamadazyma farinosa

<400> SEQUENCE: 6
aattaaccct cactaaaggg aacaaaagct ggagctccac cgcggtggcg gccgctctag    60
```

```
aactagtgga tccccgggc tgcaggaatt cggcacgagg cgtaattatg tcgttcaaaa    120
aggatcactt cacgctttcg gataacacta caattccggc cataggttac ggacttggaa    180
ccaaatggta taagcaaggg gtggataaga tagacgaaaa tgtggtgttc cacctcaagc    240
aagcaattga cgcaggtttg acacacatag atggcgcaga agtatacaac actaataggg    300
aatgcggctt ggcactcaaa aaggtggatg ttcctcgtga aaactttac attacaaaca    360 agtttatacc aaaaaatact aaggacgact cgagctctcc cttaaaagat ccatacgatg    420
cattgaagga ggatctcaaa cagttcgggg ttgactatgt gaatttatac ttgatacatt    480 gcccttcat tgaaaggag aggaacggat acacttggt ggaggcttgg aaccgtttgg    540
agaaggcgtt ggatgatggc ttaaccaaaa gcattggagt gtcgaatttc cgtgtggagg    600
atattgagga aattttgcaa tcaaagccta agtatacgcc ggttgtgaac cagattgaat    660
tcaatgcgta cttgcagaac cagaccccag gaattgttga ttattgcaaa agcataaca    720 tcttggtcga ggcttactct cccttgggtc ccgtaactaa aggcagaccg gtcctttgg    780 atgacacttt ggtcgagtta cgaagaagt ataacaagac agagtctcag attcttctta    840
gatgggtact tcagcaaggt atttttaccca tcacgacttc ttcgaacaag gaacgtctcg    900
tgcaaagtct cgaaattttc aacttcgacc                                     930

<210> SEQ ID NO 7
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 7
cgaggcttac tctcccttgg gt                                              22

<210> SEQ ID NO 8
<211> LENGTH: 22
<212> TYPE: DNA
<213> ORGANISM: Artificial Sequence
<220> FEATURE:
<223> OTHER INFORMATION: Designed origonucleotide primer for PCR

<400> SEQUENCE: 8
gtaatacgac tcactatagg gc                                              22

<210> SEQ ID NO 9
<211> LENGTH: 467
<212> TYPE: DNA
<213> ORGANISM: Yamadazyma farinosa

<400> SEQUENCE: 9
cgaggcttac tctcccttgg gtcccgtaac taaaggcaga ccgggtcctt tggatgacac     60
tttggtcgag ttatcgaaga agtataacaa gacagagtct cagattcttc ttagatgggt    120
acttcagcaa ggtatttttac ccatcacgac ttcttcgaac aaggaacgtc tcgtgcaaag    180
tctcgaaatt ttcaatttcg accttctaa ggaagacgtg gatactatct ccaggcttgg    240
tactcaaaag catttgagac agtattggac caatgagtac tcgaagtacg attaatgcgc    300
tataggtgaa gctggttttt atataattgg tactggaaat tattatgttt attattcaga    360
gtatattgag aagtaaataa tatgtttctt gttgctactg taaaaaaaaa aaaaaaaaac    420
cgaggggggg cccggtaccc aattcgccct atagtgagtc gtattac                  467
```

<210> SEQ ID NO 10
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 10
gccatggcta tgtcgttcaa aaagg                                          25

<210> SEQ ID NO 11
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 11
ctctagagtg ttaatcgtac ttcg                                           24

<210> SEQ ID NO 12
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 12
gatcatcata gcaggagtca t                                              21

<210> SEQ ID NO 13
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 13
gaattcaaca ccagtcagct c                                              21

<210> SEQ ID NO 14
<211> LENGTH: 786
<212> TYPE: DNA
<213> ORGANISM: Bacillus megaterium
<220> FEATURE:
<221> NAME/KEY: CDS
<222> LOCATION: (1)..(786)

<400> SEQUENCE: 14

```
atg tat aaa gat tta gaa gga aaa gta gtt gtc ata aca ggt tca tct      48
Met Tyr Lys Asp Leu Glu Gly Lys Val Val Val Ile Thr Gly Ser Ser
 1               5                  10                  15 acc ggt tta gga aaa gca atg gcg att cgt ttt gcg aca gaa aaa gct      96
Thr Gly Leu Gly Lys Ala Met Ala Ile Arg Phe Ala Thr Glu Lys Ala
             20                  25                  30 aaa gta gtt gtg aac tat cgt tcg aaa gaa gaa gaa gct aac agc gtt     144
Lys Val Val Val Asn Tyr Arg Ser Lys Glu Glu Glu Ala Asn Ser Val
         35                  40                  45 tta gaa gaa att aaa aaa gtg ggc gga gag gct att gcc gtc aaa ggt     192
Leu Glu Glu Ile Lys Lys Val Gly Gly Glu Ala Ile Ala Val Lys Gly
     50                  55                  60 gat gta aca gtt gag tct gat gtg atc aat tta gtt caa tct gct att     240
Asp Val Thr Val Glu Ser Asp Val Ile Asn Leu Val Gln Ser Ala Ile
 65                  70                  75                  80 aaa gaa ttt gga aag cta gac gtt atg att aat aac gca gga atg gaa     288
```

```
                                                                              -continued
Lys Glu Phe Gly Lys Leu Asp Val Met Ile Asn Asn Ala Gly Met Glu
            85                  90                  95 aat ccg gtt tcg tct cat gaa atg tct tta agt gat tgg aat aaa gtc    336
Asn Pro Val Ser Ser His Glu Met Ser Leu Ser Asp Trp Asn Lys Val
        100                 105                 110 att gat acg aac tta acg gga gca ttt tta ggc agc cgt gaa gcg att    384
Ile Asp Thr Asn Leu Thr Gly Ala Phe Leu Gly Ser Arg Glu Ala Ile
            115                 120                 125 aaa tat ttt gtg gaa aat gat att aag gga aca gtt att aac atg tcg    432
Lys Tyr Phe Val Glu Asn Asp Ile Lys Gly Thr Val Ile Asn Met Ser
130             135                 140 agt gtt cac gag aaa att cct tgg cca tta ttt gtt cat tac gca gca    480
Ser Val His Glu Lys Ile Pro Trp Pro Leu Phe Val His Tyr Ala Ala
145             150                 155                 160 agt aaa ggc gga atg aag ctc atg acc gaa aca ctt gca tta gaa tac    528
Ser Lys Gly Gly Met Lys Leu Met Thr Glu Thr Leu Ala Leu Glu Tyr
                165                 170                 175 gct cca aaa ggt att cgt gta aat aac att gga ccg gga gcg att aat    576
Ala Pro Lys Gly Ile Arg Val Asn Asn Ile Gly Pro Gly Ala Ile Asn
            180                 185                 190 aca ccg att aac gct gag aaa ttt gct gat cct gag cag cgt gca gat    624
Thr Pro Ile Asn Ala Glu Lys Phe Ala Asp Pro Glu Gln Arg Ala Asp
        195                 200                 205 gta gaa agc atg att cca atg gga tac att gga gag ccg gaa gaa att    672
Val Glu Ser Met Ile Pro Met Gly Tyr Ile Gly Glu Pro Glu Glu Ile
    210                 215                 220 gca gcg gtt gct gca tgg cta gct tct tca gag gca agt tat gta aca    720
Ala Ala Val Ala Ala Trp Leu Ala Ser Ser Glu Ala Ser Tyr Val Thr
225                 230                 235                 240 ggg att aca ctc ttt gct gac ggc ggt atg aca cag tac cca tca ttc    768
Gly Ile Thr Leu Phe Ala Asp Gly Gly Met Thr Gln Tyr Pro Ser Phe
                245                 250                 255 caa gca gga cgc gga taa                                             786
Gln Ala Gly Arg Gly
            260

<210> SEQ ID NO 15
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 15
gccatggcta tgtataaaga tttagaa                                       27

<210> SEQ ID NO 16
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 16
cggatccgtt atccgcgtcc tgc                                           23

<210> SEQ ID NO 17
<211> LENGTH: 24
<212> TYPE: DNA
<213> ORGANISM: Artificial Sequence
```

-continued

```
<220> FEATURE:
<223> OTHER INFORMATION: Designed oligonucleotide primer for PCR

<400> SEQUENCE: 17
cggatccgag gaaacagacc atgg                                              24
```

REDUCTASE GENE AND USE THEREOF

BACKGROUND OF THE INVENTION

1. Field of the Invention

The present invention relates to a gene coding a reductase, the enzyme, and use thereof.

2. Description of the Related Art (R)-2-hydroxy-4-phenylbutyrates are compounds useful as medical and agricultural chemical intermediates and the like, and up to now, there are suggested various production methods thereof (JP-B No. 2774341).

However, conventional (R)-2-hydroxy-4-phenylbutyrate production methods are not necessarily sufficient from the industrial standpoint, and a novel (R)-2-hydroxy-4-phenylbutyrate production method has been required.

SUMMARY OF THE INVENTION

The following genes coding a protein having an ability of asymmetrically reducing a 2-oxo-4-phenylbutyrate to produce a (R)-2-hydroxy-4-phenylbutyrate advantageously from the industrial standpoint, the protein, and methods of producing a (R)-2-hydroxy-4-phenylbutyrate using them, are provided.

That is, the present invention provides

[1]. A gene having any of the following base sequence (hereinafter, referred to as gene of the present invention in some cases):

a) a base sequence coding an amino acid sequence set out in SEQ ID NO:1, b) a base sequence of DNA having a sequence homology of at least 70% with DNA having a base sequence coding an amino acid sequence set out in SEQ ID NO:1, and the base sequence coding an amino acid sequence of a protein having an ability of asymmetrically reducing ethyl 2-oxo-4-phenylbutyrate to produce ethyl (R)-2-hydroxy-4-phenylbutyrate, c) a base sequence of DNA hybridizing under stringent condition with DNA having a base sequence coding an amino acid sequence set out in SEQ ID NO:1, and the base sequence coding an amino acid sequence of a protein having an ability of asymmetrically reducing ethyl 2-oxo-4-phenylbutyrate to produce ethyl (R)-2-hydroxy-4-phenylbutyrate, d) a base sequence set out in SEQ ID NO:2;

[2]. A gene obtained by connecting a promoter functionable in a host cell with the gene according to [1] in a functionable form.

[3]. A recombinant vector comprising the gene according to [1] or [2] (hereinafter, referred to as vector of the present invention in some cases).

[4]. A transformant obtained by introducing the gene according to [2] or the recombinant vector according to [3] into a host cell.

[5]. The transformant according to [4], wherein the host cell is a microorganism.

[6]. The transformant according to [4], wherein the host cell is E. coli.

[7]. A transformant retaining the gene according to [1] (hereinafter, referred to as transformant of the present invention in some cases).

[8]. A method of producing a transformant, comprising a process of introducing the recombinant vector according to [3] into a host cell;

[9]. A protein having any of the following amino acid sequence (hereinafter, referred to as protein of the present invention in some cases):

a) an amino acid sequence set out in SEQ ID NO:1, b) an amino acid sequence coded by a base sequence of DNA having a sequence homology of at least 70% with DNA having a base sequence set out in SEQ ID NO:2, and the amino acid sequence being an amino acid sequence of a protein having an ability of asymmetrically reducing ethyl 2-oxo-4-phenylbutyrate to produce ethyl (R)-2-hydroxy-4-phenylbutyrate, c) an amino acid sequence coded by a base sequence of DNA hybridizing under stringent condition with DNA having a base sequence set out in SEQ ID NO:2, and the amino acid sequence being an amino acid sequence of a protein having an ability of asymmetrically reducing ethyl 2-oxo-4-phenylbutyrate to produce ethyl (R)-2-hydroxy-4-phenylbutyrate, d) an amino acid sequence containing deletion, substitution or addition of one or a few of amino acids in an amino acid sequence set out in SEQ ID NO:1, the amino acid sequence being an amino acid sequence of a protein having an ability of asymmetrically reducing ethyl 2-oxo-4-phenylbutyrate to produce ethyl (R)-2-hydroxy-4-phenylbutyrate, e) an amino acid sequence having a sequence homology of at least 80% with an amino acid sequence set out in SEQ ID NO:1, and the amino acid sequence being an amino acid sequence of a protein having an ability of asymmetrically reducing ethyl 2-oxo-4-phenylbutyrate to produce ethyl (R)-2-hydroxy-4-phenylbutyrate.

[10]. A method of producing a (R)-2-hydroxy-4-phenylbutyrate, comprising allowing the protein according to [9], a transformant producing the same or its treated product to act on a 2-oxo-4-phenylbutyrate.

[11]. A recombinant vector comprising the gene according to [1] and a gene having a base sequence coding an amino acid sequence of a protein having an ability of converting oxidized β-nicotinamide adenine dinucleotide or oxidized β-nicotinamide adenine dinucleotide phosphoric acid into a reduced type.

[12]. The recombinant vector according to [11], wherein the protein having an ability of converting oxidized β-nicotinamide adenine dinucleotide or oxidized β-nicotinamide adenine dinucleotide phosphoric acid into a reduced type is a glucose dehydrogenase.

[13]. A transformant obtained by introducing the recombinant vector according to [11] or [12] into a host cell.

[14]. The transformant according to [13], wherein the host cell is a microorganism.

[15]. The transformant according to [13], wherein the host cell is E. coli.

[16]. A transformant retaining the gene according to [1] and a gene having a base sequence coding an amino acid sequence of a protein having an ability of converting oxidized β-nicotinamide adenine dinucleotide or oxidized β-nicotinamide adenine dinucleotide phosphoric acid into a reduced type.

[17]. The method of producing a (R)-2-hydroxy-4-phenylbutyrate according to [10], wherein a protein having an ability of converting oxidized β-nicotinamide adenine dinucleotide or oxidized β-nicotinamide adenine dinucleotide phosphoric acid into a reduced type is allowed to coexist in the reaction system.

[18]. The method of producing a (R)-2-hydroxy-4-phenylbutyrate according to [17], wherein the protein having an ability of converting oxidized β-nicotinamide adenine dinucleotide or oxidized β-nicotinamide adenine dinucleotide phosphoric acid into a reduced type is a glucose dehydrogenase.

[19]. A method of producing a (R)-2-hydroxy-4-phenylbutyrate, comprising allowing the transformant according to any of [13] to [15] or its treated product to act on a 2-oxo-4-phenylbutyrate.

[20]. A method of producing a (R)-2-hydroxy-4-phenylbutyrate, comprising allowing the transformant according to [16] or its treated product to act on a 2-oxo-4-phenylbutyrate.

(0006)

DETAILED DESCRIPTIONS OF PREFERRED EMBODIMENTS

First, the gene of the present invention will be described.

The gene of the present invention may be a natural gene, or a gene generated by introducing a mutation into a natural gene (partial specific mutation introduction method, mutation treatment and the like). In the case of searching a natural gene, microorganisms having an ability of asymmetrically reducing ethyl 2-oxo-4-phenylbutyrate to produce ethyl (R)-2-hydroxy-4-phenylbutyrate may advantageously be subjects, and for example, microorganisms belonging to Yamadazyma such as Yamadazyma farinosa and the like are listed as the subject.

In the gene of the present invention, "DNA hybridizing under stringent condition with DNA having a base sequence coding an amino acid sequence set out in SEQ ID NO:1" denotes DNA (1) which forms a DNA-DNA hybrid with DNA having a base sequence coding an amino acid sequence set out in SEQ ID NO:1 by hybridizing at 65° C., under high ion concentration [for example, 6×SSC (900 mM sodium chloride, 90 mM sodium citrate) is mentioned] and (2) in which the hybrid can be maintained even after temperature insulation at 65° C. for 30 minutes, under low ion concentration [for example, 0.1×SSC (15 mM sodium chloride, 1.5 mM sodium citrate) is mentioned], for example, in the Southern Hybridization method described in "Cloning and Sequence" (Watanabe Satoshi supervised, Sugiura Masahiro edited, 1989, Noson Bunka sha published) and the like.

Specifically mentioned are, for example, DNA composed of a base sequence coding an amino acid sequence set out in SEQ ID NO:1, DNA composed of a base sequence containing deletion, substitution or addition of partial bases in a base sequence coding an amino acid sequence set out in SEQ ID NO:1, DNA having a sequence homology of at least 70%, preferably at least 80%, more preferably at least 90%, further preferably at least 95%, most preferably at least 99% with DNA composed of a base sequence coding an amino acid sequence set out in SEQ ID NO:1, and the like.

Such DNA may be DNA cloned from DNAs present in the natural field, DNA containing artificially introduced deletion, substitution or addition of partial bases in a base sequence of this cloned DNA, or artificially synthesized DNA. Sequence homology can be calculated using sequence analyzing tools such as, for example, UWGCG Package-supplied BESTFIT program (Devereux et al (1984) Nucleic Acids Research 12, p. 387-395), PILEUP, BLAST algorithm (Altschul S. F. (1993) J Mol Evol 36: 290-300; Altschul S. F. (1990) J Mol Biol 215: 403-10), and the like.

DNA of the gene of the present invention can be prepared, for example, as follows.

A cDNA library is prepared according to a usual gene engineering technique (for example, method described in "Shin Saibokogaku Jikken Protocol" (published by Tokyo University, Medical Science Laboratory, Oncology Research Department; Shujunsha, 1993)) from microorganisms belonging to Yamadazyma genus such as Yamadazyma farinose and the like, and PCR is performed using the prepared cDNA library as a template and using an appropriate primer, thereby amplifying DNA composed of a base sequence coding a amino acid sequence set out in SEQ ID NO:1, DNA composed of a base sequence coding an amino acid sequence containing deletion, substitution or addition of one or a few of amino acids in an amino acid sequence set out in SEQ ID NO:1 and/or DNA having a base sequence set out in SEQ ID NO:2, and the like, thus, DNA of the gene of the present invention can be prepared.

Further, PCR is performed using, as a template, the above-mentioned cDNA library, and using, as a primer, an oligonucleotide having a base sequence set out in SEQ ID NO:10 and an oligonucleotide having a base sequence set out in SEQ ID NO:11, thereby amplifying DNA composed a base sequence set out in SEQ ID NO:2, thus, DNA of the gene of the present invention can be prepared.

The condition of the PCR includes, for example, a condition in which a reaction solution obtained by mixing 4 kinds of DNTPs each in an amount of 20 μM, 2 kinds of oligonucleotide primers each in an amount of 15 pmol, Taqpolymerase in an amount of 1.3 U and a cDNA library as a template is heated at 97° C. (for 2 minutes), then, a cycle of 97° C. (for 0.25 minutes)-50° C. (for 0.5 minutes)-72° C. (for 1.5 minutes) is repeated 10 times, then, a cycle of 97° C. (for 0.25 minutes)-55° C. (for 0.5 minutes)-72° C. (for 2.5 minutes) is repeated 20 times, further, the reaction solution is kept at 72° C. for 7 minutes.

A restriction enzyme recognition sequence or the like may be added to the 5' end side and/or the 3' end side of a primer used for the PCR.

It is also possible to perform PCR using, as a template, the above-mentioned cDNA library and using, as a primer, an oligonucleotide having a partial base sequence selected from base sequences coding an amino acid sequence set out in SEQ ID NO:1 (for example, oligonucleotide composed of a base sequence of about 14 bases or more at the 5' end side coding an amino acid sequence set out in SEQ ID NO:1) and an oligonucleotide of about 14 bases or more composed of a base sequence complementary to a base sequence near a DNA insertion site of a vector used for generating a cDNA library, thereby amplifying DNA having a base sequence coding an amino acid sequence set out in SEQ ID NO:1, DNA having a base sequence coding an amino acid sequence containing deletion, substitution or addition of one or a few of amino acids in an amino acid sequence set out in SEQ ID NO:1, and the like, to prepare DNA of the gene of the present invention.

DNA amplified as described above can be cloned to a vector according to a method described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like, to obtain the recombinant vector of the present invention. Specific examples of the vector to be used include pUC119 (manufactured by Takara Shuzo Co., Ltd.), pTV118N (Takara Shuzo Co., Ltd.), pBluescriptII (Toyobo Co., Ltd.), pCR2.1-TOPO (Invitrogen), pTrc99A (Pharmacia), pKK223-3 (Pharmacia) and the like.

DNA of the gene of the present invention can also be obtained by hybridizing, under conditions described later, DNA as a probe composed of a base sequence of about 15 bases or more having a partial base sequence selected from base sequences coding an amino acid sequence set out in SEQ ID NO:1, with a cDNA library inserted into a microorganism- or phage-derived vector, and detecting DNA to which the probe bonds specifically.

As the method of hybridizing a probe with chromosomal DNA or cDNA, for example, colony hybridization and plaque hybridization are mentioned, and the method can be selected according to the kind of a vector used for generating a library.

When a library to be used is generated using a plasmid vector, it is recommendable to use colony hybridization. Specifically, DNA of a library is introduced into a host microorganism to obtain a transformant, the resulting transformant is diluted, then, the diluted product is inoculated on an agar medium, and culturing is performed until appearance of a colony.

When a library to be used is generated using a phage vector, it is recommendable to use plaque hybridization. Specifically, a host microorganism and a phage of a library are mixed under infectable condition, further mixed with a soft agar medium, then, the mixture is inoculated on an agar medium, and culturing is performed until appearance of a plaque.

Then, in any hybridization cases, a membrane is placed on the agar medium on which the above-mentioned culturing has been effected, and a transformant or phage is adsorbed and transferred to the membrane. This membrane is treated with an alkali, then, neutralized, then, DNA is fixed to the membrane. More specifically, for example, in the case of plaque hybridization, a nitrocellulose membrane or nylon membrane (for example, Hybond-N$^+$ (registered trademark of Amersham)) is placed on the above-mentioned agar medium, and allowed to stand still for about 1 minute to cause adsorption and transferred of phage particles to a membrane. Then, the membrane is immersed in an alkali solution (for example, 1.5 M sodium chloride, 0.5 M sodium hydroxide) for about 3 minutes to cause dissolution of phage particles, thereby, eluting phage DNA on a membrane, then, immersed in a neutralization solution (for example, 1.5 M sodium chloride, 0.5 M Tris-hydrochloric acid buffering solution, pH 7.5) for about 5 minutes. Then, the membrane is washed with a washing solution (for example, 0.3 M sodium chloride, 30 mM citric acid, 0.2 M Tris-hydrochloric acid buffering solution, pH 7.5) for about 5 minutes, then, for example, heated at about 80° C. for about 90 minutes, to fix phage DNA on the membrane.

Using thus prepared membrane, hybridization is carried out using the above-mentioned DNA as a probe. Hybridization can be conducted, for example, according to descriptions of J. Sambrooke, E. F. Frisch, T. Maniatis, "Molecular Cloning: A Laboratory Manual 2nd edition (1989)", Cold Spring Harbor Laboratory Press, and the like.

DNA used as a probe may be that labeled with a radioisotope, or that labeled with a fluorescent coloring matter.

As the method of labeling DNA used as a probe with a radioisotope, there is, for example, a method of performing PCR using, as a template, DNA used as a probe, replacing dCTP in the PCR reaction solution by ($\alpha$-$^{32}$P)dCTP, by utilizing Random Primer Labeling Kit (Takara Shuzo Co., Ltd.) and the like.

When DNA used as a probe is labeled with a fluorescent coloring matter, there can be used, for example, ECL Direct Nucleic Acid Labeling and Detection System manufactured by Amersham, and the like.

Hybridization can be performed, for example, as described below.

A prehybridization solution containing 450 to 900 mM sodium chloride and 45 to 90 mM sodium citrate, containing sodium dodecylsulfate (SDS) in a concentration of 0.1 to 1.0 wt %, containing modified non-specific DNA in a concentration of 0 to 200 µl/ml, and depending on conditions, optionally containing albumin, ficoll, polyvinylpyrrolidone and the like each in a concentration of 0 to 0.2 wt % (preferably, prehybridization solution containing 900 mM sodium chloride, 90 mM sodium citrate, 1.0 wt % SDS and 100 µl/ml modified Calf-thymus DNA) is prepared in a proportion of 50 to 200 µl per 1 cm$^2$ of a membrane produced as described above, and the above-mentioned membrane is immersed in the prehybridization solution and kept at 42 to 65° C. for 1 to 4 hours.

Next, for example, a prehybridization solution containing 450 to 900 mM sodium chloride and 45 to 90 mM sodium citrate, containing SDS in a concentration of 0.1 to 1.0 wt %, containing modified non-specific DNA in a concentration of 0 to 200 µl/ml, and depending on conditions, optionally containing albumin, ficoll, polyvinylpyrrolidone and the like each in a concentration of 0 to 0.2 wt % (preferably, prehybridization solution containing 900 mM sodium chloride, 90 mM sodium citrate, 1.0 wt % SDS and 100 µg/ml modified Calf-thymus DNA) is mixed with a probe prepared by the above-mentioned method (amount corresponding to $1.0 \times 10^4$ to $2.0 \times 10^6$ cpm per 1 cm$^2$ of membrane) to give a solution which is prepared in a proportion of 50 to 200 µl per 1 cm$^2$ of the membrane, and the membrane is immersed in the hybridization solution and kept at 42 to 65° C. for 12 to 20 hours.

After the hybridization, the membrane is taken out, and washed using a washing solution of 42 to 65° C. containing 15 to 300 mM sodium chloride, 1.5 to 30 mM sodium citrate and 0.1 to 1.0 wt % SDS and the like (preferably, washing solution of 65° C. containing 15 mM sodium chloride, 1.5 mM sodium citrate and 1.0 wt % SDS). The washed membrane is rinsed slightly with 2×SSC (300 mM sodium chloride, 30 mM sodium citrate), then, dried. This membrane is subjected to, for example, autoradiography and the like to detect a position of a probe on the membrane, thereby specifying, on the original agar medium, a clone hybridizing with a probe used and corresponding to a position of DNA on the membrane, and this is picked up to isolate a clone having the DNA.

DNA of the gene of the present invention can be prepared from a cultured cell obtained by culturing thus obtained clone.

DNA prepared as described above can be cloned to a vector according to a method described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like, to obtain the recombinant vector of the present invention. Specific examples thereof include pUC119 (manufactured by Takara Shuzo Co., Ltd.), pTV118N (Takara Shuzo Co., Ltd.), pBluescriptII (Toyobo Co., Ltd.), pCR2.1-TOPO (Invitrogen), pTrc99A (Pharmacia), pKK223-3 (Pharmacia) and the like.

The above-mentioned DNA base sequence can be analyzed by a dideoxy terminator method described in F. Sanger, S. Nicklen, A. R. Coulson, Proceeding of Natural Academy of Science U.S.A. (1977) 74: 5463-5467, and the like. For preparing a sample for base sequence analysis, commercially available reagents such as, for example, ABI PRISM Dye Terminator Cycle Sequencing Ready Reaction Kit manufactured by Perkin Elmer, and the like may be used.

Confirmation of a fact that DNA obtained as described above is coding an amino acid sequence of a protein having an ability of asymmetrically reducing ethyl 2-oxo-4-phenylbutyrate to produce ethyl (R)-2-hydroxy-4-phenylbutyrate can be performed, for example, as described below.

First, DNA obtained as described above is inserted into a vector so as to be connected to a downstream site of a promoter which is functionable in a host cell, and this vector is introduced into a host cell, to obtain a transformant. Then, a cultured product of the transformant is allowed to act on ethyl 2-oxo-4-phenylbutyrate. By analyzing the amount of ethyl (R)-2-hydroxy-4-phenylbutyrate, a fact that the resulting DNA codes an amino acid sequence of a protein having such ability can be confirmed.

For allowing the gene of the present invention to express in a host cell, for example, a gene prepared by connecting a promoter which is functionable in a host cell to the gene of the present invention, in a functionable form, is introduced into a host cell.

Here, "in a functionable form" means that when a host cell is transformed by introducing the gene into the host cell, the gene of the present invention is under condition of bonding to a promoter so as to be expressed under control of the promoter. As the promoter, mentioned are a promoter of lactose operon of *E. Coli*, a promoter of tryptophan operon of *E. Coli*, or, synthetic promoters which are functionable in *E. Coli* such as tac promoter, trc promoter and the like. A promoter controlling expression of the gene of the present invention in Yamadazyma farinosa may be utilized.

In general, a recombinant vector obtained by incorporation of a gene connected in a functionable form to a promoter functionable in a host cell, into a vector as described above, is introduced into a host cell. When a vector containing a selective marker gene (antibiotic resistance imparted gene such as, for example, kanamycin-resistant gene, neomycin-resistant gene and the like) is used as the vector, a transformant containing the vector introduced can be selected utilizing the phenotype of the selective marker gene and the like as an index.

As the host cell into which the gene of the present invention or the recombinant vector of the present invention connected in a functionable form to a promoter functionable in a host cell is introduced, mentioned are microorganisms belonging to, for example, *Escherichia* genus, *Bacillus* genus, *Corynebacterium* genus, *Staphylococcus* genus, *Streptomyces* genus, *Saccharomyces* genus, *Kluyveromyces* genus, *Pichia* genus, *Rhodococcus* genus and *Aspergillus* genus.

The method of introducing the gene of the present invention or the recombinant vector of the present invention connected in a functionable form to a promoter functionable in a host cell, into a host cell, may be an introduction method usually used depending on the host cell to be used, and mentioned are, for example, a calcium chloride method described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like, an electroporation method described in "Methods in Electroporation: Gene Pulser/*E. coli* Pulser System" Bio-Rad Laboratories (1993), and the like.

For selecting the transformant into which the gene of the present invention or the recombinant vector of the present invention connected in a functionable form to a promoter functionable in a host cell is introduced, for example, it is recommendable to select the transformant utilizing the phenotype of a selective marker gene contained in a vector as described above as an index.

A fact that the transformant retains the gene of the present invention can be confirmed by performing recognition of a restriction enzyme site, analysis of a base sequence, Southern Hybridization, Western Hybridization and the like, according to usual methods described in "Molecular Cloning: A Laboratory Manual 2nd edition" (1989), Cold Spring Harbor Laboratory Press, and the like.

Next, the protein of the present invention will be described.

"Amino acid sequence containing deletion, substitution or addition of one or a few of amino acids in an amino acid sequence set out in SEQ ID NO:1" means an amino acid sequence coding a protein having the same activity in nature, and having a sequence homology of at least 80%, preferably at least 90%, more preferably at least 95%, further preferably at least 99% with a whole amino acid sequence set out in SEQ ID NO:1.

The protein of the present invention can be produced by, for example, culturing a transformant retaining the gene of the present invention.

As the medium for culturing the transformant, various media appropriately containing carbon sources, nitrogen sources, organic salts, inorganic salts and the like usually used for culturing of a host cell of a microorganism and the like, for example, can be used.

Examples of the carbon source include saccharides such as glucose, dextrin, sucrose and the like, sugar alcohols such as glycerol and the like, organic acids such as fumaric acid, citric acid, pyruvic acid and the like, animal oils, vegetable oils and molasses. The addition amount of these carbon sources to a medium is usually about 0.1 to 30% (w/v) based on culturing liquid.

Examples the nitrogen source include natural organic nitrogen sources such as meat extract, peptone, yeast extract, malt extract, soybean powder, Corn Steep Liquor, cotton seed powder, dry yeast, casamino acid and the like, amino acids, sodium salts of inorganic acids such as sodium nitrate and the like, ammonium salts of inorganic acids such as ammonium chloride, ammonium nitrate, ammonium phosphate and the like, ammonium salts of organic acids such as ammonium fumarate, ammonium citrate and the like, and urea. of them, ammonium salts of organic acids, natural organic nitrogen sources, amino acids and the like, can be used also as the carbon source in many cases. The addition amount of these nitrogen sources to a medium is usually about 0.1 to 30% (w/v) based on culturing liquid.

Examples of the organic salt and the inorganic salt include chlorides, nitrates, acetates, carbonates and phosphates of potassium, sodium, magnesium, iron, manganese, cobalt, zinc and the like. Specific examples thereof include sodium chloride, potassium chloride, magnesium sulfate, ferrous sulfate, manganese sulfate, cobalt chloride, zinc sulfate, copper sulfate, sodium acetate, calcium carbonate, monopotassium hydrogen phosphate and dipotassium hydrogen phosphate. The addition amount of these organic salts and/or inorganic salts to a medium is usually about 0.0001 to 5% (w/v) based on culture medium.

Further, in the case of a transformant containing an introduced gene in which a promoter of type derived by allolactose such as tac promoter, trc promoter, lac promoter and the like, and the gene of the present invention are connected in a functionable form, for example, isopropyl thio-β-D-galactoside (IPTG) can also be added in small amount into a medium, as an inducer for inducing production of the protein of the present invention.

Culturing of a transformant retaining the gene of the present invention can be carried out according to a method usually used for culturing of a host cell of a microorganism and the like, and examples thereof include liquid culture and solid culture such as test tube shaking type culture, reciprocating type shaking culture, jar Fermenter culturing, tank culture and the like.

The cultivating temperature can be appropriately altered in a range in which the transformant can grow, and it is usually about 15 to 40° C. pH of a medium is preferably in a range of about 6 to 8. The culturing time differs depending on the culture condition, and usually, about 1 to 5 days are preferable.

As the method of purifying the protein of the present invention from a cultured product of a transformant retaining the gene of the present invention, methods used in usual protein purification can be applied, and for example, the following methods are mentioned.

First, cells are collected from a cultured product of a transformant by centrifugal separation and the like, then, these are disrupted by physical disrupting methods such as ultrasonic treatment, dynomill treatment, French press treatment and the like or chemical disrupting methods using a surfactant or bacteriolysis enzyme such as lysozyme and the like. Impurities are removed from the resulting disrupted liquid by centrifugal separation, membrane filter filtration and the like to prepare cell-free extract, and this is fractioned appropriately using separation and purification methods such as cation exchange chromatography, anion exchange chromatography, hydrophobic chromatography, gel filtration chromatography, metal chelate chromatography and the like, thus, the protein of the present invention can be purified.

As the carrier to be used in chromatography, there are mentioned, for example, insoluble polymer carriers such as cellulose, dextrin and agarose containing a carboxymethyl (CM) group, diethylaminoethyl (DEAE) group, phenyl group or butyl group introduced, and the like. Commercially available carrier-filled columns can also be used, and examples of such commercially available carrier-filled columns include Q-Sepharose FF, Phenyl-Sepharose HP (trade names, both are manufactured by Amersham Pharmacia Biotech), TSK-gel G3000SW (trade name, manufactured by Toso Co., Ltd.), and the like.

For selecting a fraction containing the protein of the present invention, it is recommendable to select a fraction using, as an index, an ability of asymmetrically reducing ethyl 2-oxo-4-phenylbutyrate to produce preferentially ethyl (R)-2-hydroxy-4-phenylbutyrate.

Next, the method of producing a (R)-2-hydroxy-4-phenylbutyrate in the present invention will be described. This production method is that the protein of the present invention, a transformant producing the same, or its treated product is allowed to act on a 2-oxo-4-phenylbutyrate.

As the 2-oxo-4-phenylbutyrate, compounds of the following formula (1) are exemplified.

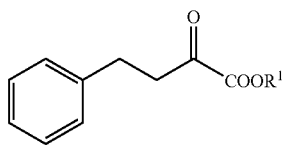

(1)

(wherein, $R^1$ represents a C1 to C8 alkyl group such as, for example, methyl, ethyl, propyl, butyl, pentyl, hexyl, heptyl, octyl and the like)

Specific examples of the 2-oxo-4-phenylbutyrate include methyl 2-oxo-4-phenylbutyrate, ethyl 2-oxo-4-phenylbutyrate, propyl 2-oxo-4-phenylbutyrate, octyl 2-oxo-4-phenylbutyrate, and the like. These esters can be produced by a method described in Tetrahedron (1985) 41(2) 467-72, or according to this method. As the (R)-2-hydroxy-4-phenylbutyrate, exemplified are C1 to C8 alkyl ester compounds of (R)-2-hydroxy-4-phenylbutyric acid in which an oxo group at 2-position of a compound of the formula (1) is asymmetrically reduced into a hydroxyl group.

The above-mentioned method is usually conducted in the presence of water and reduced nicotinamide adenine dinucleotide (hereinafter, referred to as NADH) or reduced nicotinamide adenine dinucleotide phosphoric acid (hereinafter, referred to as NADPH). The water used in this procedure may be a buffering aqueous solution. As the buffering agent to be used in the buffering aqueous solution, for example, alkali metal phosphates such as sodium phosphate, potassium phosphate and the like, alkali metal acetates such as sodium acetate aqueous solution, potassium acetate and the like, and mixtures thereof, are mentioned.

In the above-mentioned method, it is also possible to allow an organic solvent to coexist in addition to water. Examples of the organic solvent capable of coexisting include ethers such as t-butyl methyl ether, diisopropyl ether, tetrahydrofuran and the like, esters such as ethyl formate, ethyl acetate, propyl acetate, butyl acetate, ethyl propionate, butyl propionate and the like, hydrocarbons such as toluene, hexane, cyclohexane, heptane, isooctane and the like, alcohols such as methanol, ethanol, 2-propanol, butanol, t-butyl alcohol and the like, organic sulfur compounds such as dimethyl sulfoxide and the like, ketones such as acetone and the like, nitrites such as acetonitrile and the like, and mixtures thereof.

The reaction in the above-mentioned method is performed, for example, by mixing water, 2-oxo-4-phenylbutyrate, and NADH or NADPH by stirring, shaking and the like together with the protein of the present invention, a transformant producing the same or its treated product, if necessary, under condition of further containing an organic solvent and the like.

pH in reacting in the above-mentioned method can be appropriately selected, and it is usually in a range of pH 3 to 10. The reaction temperature can be appropriately selected, and from the standpoints of stability of raw materials and product, and reaction speed, it is usually in a range of 0 to 60° C.

The end point of the reaction can be determined by tracing the amount of a 2-oxo-4-phenylbutyrate in the reaction liquid by liquid chromatography and the like.

The reaction time can be appropriately selected, and usually, it is in a range of 0.5 hours to 10 days.

Recovering of a (R)-2-hydroxy-4-phenylbutyrate from the reaction liquid may be carried out by generally known any methods.

Mentioned are methods of purifying by effecting post treatments such as an operation of extracting an organic solvent of reaction liquid, a concentration operation and the like, if necessary, combining column chromatography, distillation and the like.

The protein of the present invention, a transformant producing the same or its treated product can be used in various forms in the above-mentioned method.

Examples of specific forms include a cultured product of a transformant retaining the gene of the present invention, treated product of such a transformant, cell-free extract, crude extract, purified protein and the like, and immobilized products thereof. Here, examples of the treated product of a transformant include a lyophilized transformant, organic solvent-treated transformant, dry transformant, transformant-disrupted product, autolysate of transformant, ultrasonic-treated product of transformant, transformant extracted product, and alkali-treated product of transformant. As the method of obtaining an immobilized product, mentioned are, for example, a carrier bonding method (method of adsorbing the protein of the present invention and the like to an inorganic carrier such as silica gel, ceramic and the like, cellulose, ion exchange resin and the like) and an entrapping method (method of entrapping the protein of the present invention and the like into a network structure of a polymer such as polyacrylamide, sulfur-containing polysaccharide gel (e.g., carrageenan gel), alginic acid gel, agar gel and the like).

In considering industrial production using a transformant retaining the gene of the present invention, a method of using an sterilized product of the transformant is more preferable because of little restriction on production equipments than a method using a live transformant. As the sterilization method for this, for example, physical sterilization methods (heating, drying, freezing, beam, ultrasonic wave, filtration, power distribution), and sterilization methods using chemical drugs (alkali, acid, halogen, oxidizer, sulfur, boron, arsenic, metal, alcohol, phenol, amine, sulfide, ether, aldehyde, ketone, cyan and antibiotic) are mentioned. In general, it is desirable to select treatment methods which do not deactivate as much as possible enzymatic activity of the protein of the present invention and cause little influence on remaining in the reaction system, pollution and the like, among these sterilization methods.

The method of producing a (R)-2-hydroxy-4-phenylbutyrate of the present invention is carried out in the presence of NADH or NADPH, and with progress of an asymmetric reduction reaction of a 2-oxo-4-phenylbutyrate, the NADH or NADPH is converted into oxidized β-nicotinamide adenine dinucleotide (hereinafter, referred to as $NAD^+$) or oxidized β-nicotinamide adenine dinucleotide phosphoric acid (hereinafter, referred to as $NADP^+$). The $NAD^+$ or $NADP^+$ generated by conversion can be returned into the original NADH or NADPH by a protein having an ability of converting $NAD^+$ or $NADP^+$ into a reduced type (NADH or NADPH), therefore, it is also possible to allow a protein having an ability of converting $NAD^+$ or $NADP^+$ into NADH or NADPH to coexist in the reaction system of the above-mentioned method.

As the protein having an ability of converting $NAD^+$ or $NADP^+$ into NADH or NADPH, for example, glucose dehydrogenases, alcohol dehydrogenases, aldehyde dehydrogenases, amino acid dehydrogenases and organic dehydrogenases (malic acid dehydrogenase and the like) and the like are mentioned.

When the protein having an ability of converting $NAD^+$ or $NADP^+$ into NADH or NADPH is a glucose dehydrogenase, the activity of the protein is reinforced in some cases by coexistence of glucose and the like in the reaction system, and for example, these may be added to the reaction liquid.

The protein may be an enzyme itself, or may coexist in the reaction system in the form of a microorganism having the enzyme or a treated product of the microorganism. Further, it may be a transformant or its treated product containing a gene having a base sequence coding an amino acid sequence of a protein having an ability of converting $NAD^+$ or $NADP^+$ into NADH or NADPH. Here, the treated product means that equivalent to "treated product of a transformant" described above.

The method of producing a (R)-2-hydroxy-4-phenylbutyrate of the present invention can also be carried out using a transformant retaining simultaneously genes having a base sequence coding an amino acid sequence of a protein having an ability of converting $NAD^+$ or $NADP^+$ into NADH or NADPH such as glucose dehydrogenases, alcohol dehydrogenases, aldehyde dehydrogenases, amino acid dehydrogenases and organic dehydrogenases (malic acid dehydrogenase and the like) and the like.

As the method of introducing both genes into a host cell in this transformant, there are mentioned, for example, a method of introducing a single vector containing both genes into a host cell, a method of transforming a host cell with recombinant vectors prepared by introducing both genes separately into several vectors of different origins, and the like. Further, one gene or both genes may also be introduced into the chromosome of a host cell.

In the method of introducing a single vector containing both genes into a host cell, for example, regions correlated with expression control such as a promoter, terminator and the like may be connected to both genes to generate a recombinant vector, or a recombinant vector may be generated which is expressed as an operon containing a few of cistrons such as lactose operon.

According to the present invention, genes coding a protein having an ability of producing a (R)-2-hydroxy-4-phenylbutyrate advantageously from the industrial standpoint, the protein, and methods of producing a (R)-2-hydroxy-4-phenylbutyrate using them, are provided.

EXAMPLES

The present invention will be illustrated further specifically by the following examples and the like, but the present invention is not limited to these examples at all.

Reference Example 1

Preparation of cDNA Library (A)

Into two 500 ml flasks were placed a medium (2 g of glucose, 0.5 g of polypeptone, 0.3 g of yeast extract and 0.3 g of malt extract were dissolved in 100 ml of water, and pH was adjusted to 6 with 2 N HCl) each in an amount of 100 ml, and the flasks were sterilized at 121° C. for 15 minutes. Into these flasks were added culture medium of Yamadazyma farinose IF0193 strain cultured (30° C., 48 hours, shaking culturing) in a medium of the same composition each in an amount of 0.3 ml, and cultured at 30° C. for 72 hours while shaking. Thereafter, the resulting culture medium was centrifuged (8000 rpm, 10 minutes), and the resulting precipitate was collected. This precipitate was washed with 50 ml of 0.85% saline, to obtain 3.64 g of wet cell.

Using this cell, whole RNA was prepared by a guanidine thiocyanate phenolchloroform method. Further, RNA having poly(A) was obtained using Oligotex-dT30<Super>mRNA purification kit (manufactured by Takara Shuzo Co., Ltd.) from the whole RNA.

Generation of a cDNA library was performed as described below based on Gubler and Hoffman method. Single stranded cDNA was prepared using the above-mentioned RNA (3.0 µg) having poly(A), and Oligo(dT) 18-anchor primer ((Xhol-containing site) Takara Shuzo Co. Ltd.), RAV-2, Rtase and SuperScriptII Rtase, and to this reaction solution (containing single stranded cDNA prepared) was added E. coli DNA polymerase, E. coli Rnase/E. coli DNA Ligase Mixture and T4 DNA Polymerase, and synthesis of double stranded cDNA and blunt end formation were performed. Then, ligation of this double stranded cDNA with EcoRl-Notl-BamHl adaptor (manufactured by Takara Shuzo Co., Ltd.) was conducted. DNA after ligation was phosphorylated, cut with Xhol, low molecular weight DNA was removed by a spin column (manufactured by Takara Shuzo Co., Ltd.) and ligation with λZapll (EcoRl-Xhol cut) was carried out, then, packaging was performed using MaxPlax Lambda Packaging Extracts (manufactured by EPICENTRE) to obtain a cDNA library (hereinafter, referred to as cDNA library (A)).

Reference Example 2

Preparation of Intracellular DNA (B)

In the same manner as in Reference Example 1, 1.8 g of wet cell of Yamadazyma farinose IF0193 strain was obtained.

From the above-mentioned cell, intracellular DNA (hereinafter, referred to as intracellular DNA (B)) was obtained using QIAprep Genomic-tip System (manufactured by Qiagen).

Example 1

Obtaining of Gene of the Present Invention and Analysis Thereof (1) Preparation of Protein of the Present Invention About 62 g of wet cell of Yamadazyma farinose IF0193 strain prepared under the same conditions as in Reference Example was suspended in 120 ml of 20 mM potassium phosphate buffer (pH 7.0), and disrupted by a multi beads shocker (manufactured by Yasui Kikai, glass beads 0.5 mmF, 2500 rpm, 10 minutes). The resulting disrupted liquid was centrifugally separated (10000×g, 10 minutes), and the supernatant was ultracentrifugally separated (100000×g, 60 minutes), to obtain about 150 ml of ultracentrifuged supernatant.

About 150 ml of the resulting ultracentrifuged supernatant was concentrated using Amicon Ultra-15 (manufactured by MILLIPORE), and the buffer was substituted by 20 mM Tris-HCl buffer (pH 8.5). This was applied to an ion exchange chromatography column [HiTrap DEAE Sepharose FF (manufactured by Amersham Farmacia Biotech)][equilibrated with Tris-HCl buffering solution (20 mM, pH 8.5)], and eluted using, as a mobile bed, Tris-HCl buffering solution containing dissolved sodium chloride (concentration gradient of 0→0.5 M of sodium chloride concentration), to obtain 15 ml of a fraction having a sodium chloride concentration of 0.01 to 0.15 M as a fraction having reductase activity.

This eluted fraction was concentrated using Amicon Ultra-15 (manufactured by MILLIPORE), and de-salted, and the buffer was substituted by 20 mM sodium phosphate buffer (pH 7.0). This was applied to an affinity chromatography column [HiTrap BlueHP (manufactured by Amersham Farmacia Biotech)] [equilibrated with 20 mM sodium phosphate buffer (pH 7.0)], and eluted using, as a mobile bed, sodium phosphate buffering solution containing dissolved sodium chloride (concentration gradient of 0→1.0 M of sodium chloride concentration), to obtain 8 ml of a fraction having a sodium chloride concentration of 0.48 to 0.67 M as a fraction having reductase activity.

This eluted fraction was concentrated using Amicon Ultra-15 (manufactured by MILLIPORE), and de-salted, and the buffer was substituted by 0.1 M potassium phosphate buffer (pH 7.0) containing 1.5 M ammonium sulfate. This was applied to a hydrophobic interaction chromatography column [RESOURCE PHE (manufactured by Amersham Farmacia Biotech)][equilibrated with 0.1 M potassium phosphate buffer (pH 7.0) containing 1.5 M ammonium sulfate], and eluted using, as a mobile bed, potassium phosphate buffering containing dissolved ammonium sulfate (concentration gradient of 1.5→0 M of ammonium sulfate concentration), to obtain 1.5 ml of an eluted fraction having an ammonium sulfate concentration of around 1.0 M as a fraction having reductase activity.

This eluted fraction was concentrated using Amicon Ultra-15 (manufactured by MILLIPORE), and de-salted, and the buffer was substituted by 50 mM sodium phosphate buffer (pH 7.0) containing 0.15 M sodium chloride. This concentrated liquid was applied to a gel filtration column [Superdex200 10/300GL (manufactured by Amersham Farmacia Biotech)] [mobile bed: 50 mM sodium phosphate buffer (pH 7.0) containing 0.15 M sodium chloride], to obtain 1 ml of an eluted fraction having a molecular weight of about 30000 dalton as a fraction having reductase activity (hereinafter, referred to as active fraction (A)).

Regarding the fraction obtained by chromatography and the like, reductase activity was measured by the following operation.

To 0.19 ml of a phosphate buffering solution (0.1 M, pH 7.0) containing dissolved ethyl 2-oxo-4-phenylbutyrate (2.06 mg/ml) and NADH (0.355 mg/ml) was added 0.01 ml of the eluted fraction obtained by chromatography and the like to give a total amount of 0.2 ml, the mixture was thermally kept at 37° C. for 20 seconds, then, the absorbance at 340 nm was measured. From the absorbance at 340 nm, the consumption amount of NADH was calculated to obtain the reductase activity of the fraction.

(2) Analysis of Amino Acid Sequence in Partial Peptide Derived from Protein of the Present Invention The active fraction (A) obtained by the above-mentioned operation was subjected to SDS polyacrylamide gel electrophoresis according to a method described in Laemmli, U. K., Nature, (1970) 227, 680. The gel after electrophoresis was stained with Coomassie Brilliant Blue G250 staining liquid (manufactured by BIO-RAD), and the gel at the stained part was cut. This gel was washed, then, trypsin-treated, and a peptide was extracted from the gel. The extracted peptide was preparative-isolated by HPLC (column: TSK gel ODS-80Ts, 2.0 mm×250 mm (Toso Co., Ltd.), mobile bed: A liquid (0.1% trifluoroacetic acid water), B liquid (90% acetonitrile aqueous solution containing 0.09% trifluoroacetic acid), concentration gradient: A/B =100/0→0/100). Regarding one fraction from the preparative-isolated fractions, an amino acid sequence was determined by Protein Sequencer (Procise 494HT Protein Sequencing System). The determined amino acid sequence is shown in SEQ ID NO:3.

(3) Analysis of Partial Base Sequence Derived From Gene of the Present Invention (part 1)

Based on the amino acid sequence shown in SEQ ID NO:3, an oligonucleotide primer having a base sequence shown in SEQ ID NO:4 was synthesized. Based on a base sequence near DNA insertion site of the vector used for generation of a cDNA library, an oligonucleotide primer having a base sequence shown in SEQ ID NO:5 was synthesized.

Using the oligonucleotide primers having base sequences shown in SEQ ID NO:4 and SEQ ID NO:5, PCR was carried out under the following reaction solution composition and reaction condition using the above-mentioned cDNA library (A) as a template (using Expand High Fidelity PCR System, manufactured by Roche Diagnostics).

[Reaction Solution Composition]

| | |
|---|---|
| cDNA library stock solution | 1 μl |
| dNTP (each 2.5 mM-mix) | 4 μl |
| primer (50 pmol/μl) | each 0.3 μl |

-continued

| | |
|---|---|
| 10× buffer (with MgCl) | 5 μl |
| enz.expand HiFi (3.5 × 10³ U/ml) | 0.75 μl |
| ultrapure water | 38.65 μl |

[Reaction Condition]

A vessel containing a reaction solution of the above-mentioned composition was set on PERKIN ELMER-GeneAmp PCR System 9700, and heated at 94° C. (2 minutes), then, a cycle of 94° C. (0.25 minutes)-55° C. (0.5 minutes)-72° C. (1.0 minute) was repeated 10 times, then, a cycle of 94° C. (0.25 minutes)-55° C. (0.5 minutes)-72° C. (1.0 minute +5 seconds/cycle) was repeated 20 times, further, the reaction solution was kept at 72° C. for 7 minutes.

Thereafter, a part of the PCR reaction solution was collected and subjected to agarose gel electrophoresis, to detect a band of a DNA fragment of about 930 bp.

The above-mentioned DNA fragment of about 930 bp was ligated to the existence "PCR Product insertion site" of pCR2.1-TOPO vector (using TOPO™TA cloning kit manufactured by Invitrogen), and in the resulting ligation liquid, E.coli TOP10F' was transformed.

On a LB (1% Bacto-trypsin, 0.5% Bacto-yeast extract, 1% sodium chloride) agar medium containing 50 μg/ml ampicillin, 30 μl of 5-bromo-4-chloro-3-indolyl-β-D-galactoside (hereinafter, referred to as X-gal) 4% aqueous solution and 30 μl of 0.1 M IPTG were applied, and the resulting transformant was inoculated to this and cultured. One white colony among the formed colonies was collected, and this colony was inoculated to sterilized LB medium (2 ml) containing 50 μg/ml ampicillin, and cultured in a test tube while shaking (30° C., 24 hours). From the cultured cell, a plasmid was taken out using QIAprep Spin Miniprep Kit (manufactured by Qiagen).

The base sequence of a DNA fragment inserted into the resulting plasmid was analyzed, to determine a base sequence shown in SEQ ID NO:6.

For analysis of the base sequence of a DNA fragment inserted into the plasmid, a sequence reaction was carried out using Dye Terminator Cycle sequencing FS ready Reaction Kit (manufactured by Perkin Elmer) and using each plasmid as a template, and the base sequence of the resulting DNA was analyzed by DNA sequencer 373A (manufactured by Perkin Elmer).

(4) Analysis of Partial Base Sequence Derived from Gene of the Present Invention (part 2)

Based on the base sequence shown in SEQ ID NO:6, an oligonucleotide primer having a base sequence shown in SEQ ID NO:7 was synthesized. Based on a base sequence near DNA insertion site of the vector used for generation of a cDNA library, an oligonucleotide primer having a base sequence shown in SEQ ID NO:8 was synthesized.

Using the oligonucleotide primers having base sequences shown in SEQ ID NO:7 and SEQ ID NO:8, PCR was carried out under the following reaction solution composition and reaction condition using the above-mentioned cDNA library (A) as a template (using Expand High Fidelity PLUS PCR System, manufactured by Roche Diagnostics).

[Reaction Solution Composition]

| | |
|---|---|
| cDNA library stock solution | 1 μl |
| dNTP (each 2.5 mM-mix) | 4 μl |

-continued

| | |
|---|---|
| primer (50 pmol/μl) | each 0.4 μl |
| 5× buffer (with MgCl) | 10 μl |
| Expand High Fidelity PLUS Taq polymerase | 0.5 μl (2.5 U) |
| ultrapure water | 33.7 μl |

[Reaction Condition]

A vessel containing a reaction solution of the above-mentioned composition was set on PERKIN ELMER-GeneAmp PCR System 9700, and heated at 94° C. (2 minutes), then, a cycle of 94° C. (0.25 minutes)-55° C. (0.5 minutes)-72° C. (1.5 minutes) was repeated 10 times, then, a cycle of 94° C. (0.25 minutes)-55° C. (0.5 minutes)-72° C. (1.0 minute +5 seconds/cycle) was repeated 20 times, further, the reaction solution was kept at 72° C. for 7 minutes.

Thereafter, a part of the PCR reaction solution was collected and subjected to agarose gel electrophoresis, to detect a band of a DNA fragment of about 430 bp.

The above-mentioned DNA fragment of about 430 bp was ligated to the existence "PCR Product insertion site" of pCR2.1-TOPO vector (using TOPO™TA cloning kit manufactured by Invitrogen), and in the resulting ligation liquid, E. coli TOP10F' was transformed.

On a LB agar medium containing 50 μg/ml ampicillin, 30 μl of X-gal 4% aqueous solution and 30 μl of 0.1 M IPTG were applied, and the resulting transformant was inoculated to this and cultured. One white colony among the formed colonies was collected, and this colony was inoculated to sterilized LB medium (2 ml) containing 50 μg/ml ampicillin, and cultured in a test tube while shaking (30° C., 24 hours). From the cultured cell, a plasmid was taken out using QIAprep Spin Miniprep Kit (manufactured by Qiagen).

The base sequence of a DNA fragment inserted into the resulting plasmid was analyzed, to determine a base sequence shown in SEQ ID NO:9.

For analysis of the base sequence of a DNA fragment inserted into the plasmid, a sequence reaction was carried out using Dye Terminator Cycle sequencing FS ready Reaction Kit (manufactured by Perkin Elmer) and using each plasmid as a template, and the base sequence of the resulting DNA was analyzed by DNA sequencer 373A (manufactured by Perkin Elmer).

Based on the base sequences shown in SEQ ID Nos. 6 and 9, ORF search was carried out to determine a base sequence (SEQ. ID NO:2) coding an amino acid sequence of a protein having an ability of asymmetrically reducing ethyl 2-oxo-4-phenylbutyrate to produce preferentially ethyl (R)-2-hydroxy-4-phenylbutyrate, of Yamadazyma farinose IF0193 strain. Further, based on SEQ ID NO:2, an amino acid sequence (SEQ ID NO:1) of the protein was determined.

SEQ ID NO:1 and SEQ ID NO:3 were compared, to find that the amino acid sequence shown in SEQ ID NO:3 corresponds to a part of the amino acid sequence shown in SEQ ID NO:1.

Example 2

Production of Transformant of the Present Invention and Reduction Reaction Example (Part 1)

(1) Preparation of Vector of the Present Invention

Based on the base sequence shown in SEQ ID NO:6, an oligonucleotide primer having a base sequence shown in SEQ ID NO:10 was synthesized, and based on the base sequence shown in SEQ ID NO:9, an oligonucleotide primer having a base sequence shown in SEQ ID NO:11 was synthesized.

Using the oligonucleotide primer having a base sequence shown in SEQ ID NO:10 and the oligonucleotide primer having a base sequence shown in SEQ ID NO:11 as a primer, PCR was carried out under the following reaction solution composition and reaction condition using the above-mentioned intracellular DNA (B) as a template (using Expand High Fidelity PLUS PCR System, manufactured by Roche Diagnostics).

[Reaction Solution Composition]

| | |
|---|---|
| cDNA library stock solution | 1 μl |
| dNTP (each 2.5 mM-mix) | 4 μl |
| primer (50 pmol/μl) | each 0.4 μl |
| 5× buffer (with MgCl) | 10 μl |
| Expand High Fidelity PLUS Taq polymerase | 0.5 μl (2.5 U) |
| ultrapure water | 33.7 μl |

[Reaction condition]

A vessel containing a reaction solution of the above-mentioned composition was set on PERKIN ELMER-GeneAmp PCR System 9700, and heated at 94° C. (2 minutes), then, a cycle of 94° C. (0.25 minutes)-55° C. (0.5 minutes)-72° C. (1.5 minutes) was repeated 10 times, then, a cycle of 94° C. (0.25 minutes)-55° C. (0.5 minutes)-72° C. (1.0 minute +5 seconds/cycle) was repeated 20 times, further, the reaction solution was kept at 72° C. for 7 minutes.

Thereafter, a part of the PCR reaction solution was collected and subjected to agarose gel electrophoresis, to detect a band of a DNA fragment of about 1000 bp.

To the remaining PCR reaction liquid was added 2 kinds of restriction enzymes (NcoI and XbaI), and the DNA fragment of about 1000 bp was double-digested, then, the enzymaticaly digested DNA fragment was purified.

On the other hand, plasmid vector pTrc99A (manufactured by Pharmacia) was double-digested with 2 kinds of restriction enzymes (NcoI and XbaI), and the enzymaticaly digested DNA fragment was purified.

These enzymaticaly digested DNA fragments were mixed, and ligated with T4 DNA ligase, and $E.$ $coli$ DH5α was transformed with the resulting ligation liquid.

The resulting transformant was cultured on a LB agar medium containing 50 μg/ml ampicillin, and from grown colonies, 10 colonies were selected randomly. These selected colonies were inoculated to sterilized LB media (2 ml) each containing 50 μg/ml ampicillin, and cultured in a test tube while shaking (37° C., 17 hours). From the cultured cells, plasmids were taken out using QIAprep Spin Miniprep Kit (manufactured by Qiagen). Respective parts of the taken out plasmids were double-digested with 2 kinds of restriction enzymes of EcoRI and PstI, then, subjected to electrophoresis, and it was confirmed that the above-mentioned DNA fragment of about 1000 bp was inserted into 4 plasmids among the taken out plasmids (hereinafter, this plasmid is referred to as pTrcRYF).

(2) Preparation of Transformant of the Present Invention and Reduction Reaction Example Using plasmid pTrcRYF, $E.$ $coli$ HB101 was transformed. The resulting transformant was inoculated to sterilized LB medium (100 ml) containing 0.1 mM IPTG and 50 μg/ml ampicillin, and cultured while shaking (30° C., 17 hours). The resulting culture medium was centrifugally separated to obtain 0.53 g of a wet cell. To the resulting wet cell was added 5 ml of 100 mM phosphate buffering solution (pH 7.0), further, glass beads (0.1 mm) corresponding to an amount of 5 ml were added, and cells were disrupted. After disrupting, about 3 ml of centrifuged supernatant was obtained. 10 mg of ethyl 2-oxo-4-phenylbutyrate, 250 μl of the above-mentioned centrifuged supernatant after disrupting, 50 mg of NADH and 750 μl of 100 mM phosphate buffering solution (pH 7.0) were mixed and stirred at 30° C. for 17 hours. Thereafter, to the reaction liquid was added 1 ml of ethyl acetate, then, centrifugal separation was performed to obtain an organic layer. This organic layer was subjected to content analysis by gas chromatography under the following condition, to find that the production amount of ethyl 2-hydroxy-4-phenylbutyrate is 79.7% based on the amount of ethyl 2-oxo-4-phenylbutyrate used in the reaction. The optical purity of ethyl 2-hydroxy-4-phenylbutyrate in an organic layer was measured under the following condition, to find 100% e.e. for (R) configuration.

(Content Analysis Condition)

Column: DB-1 (0.53 mm×30 m, 1.5 μm) (manufactured by J&W Scientific)

Column temperature: 50° C. (0 minute)→4° C./minute→170° C. (0 minute)→30° C./minute→290° C. (4 minutes)

Carrier gas: helium (column flow rate: 10 ml/minute)

Detector: FID (Optical Purity Measuring Condition)

Column: Chirasil-Dex-CB (0.32 mm×25 m, 0.25 μm) (manufactured by CHROMPACK)

Column temperature: 100° C. (0 minute)→2° C./minute→180° C. (0 minute)

Carrier gas: helium (column flow rate: 1.5 ml/minute)

Detector: FID

Slit ratio: 1/50

The absolute configuration of the product was determined by comparison with a standard sample of ethyl (R)-2-hydroxy-4-phenylbutyrate.

Example 3

Production of Transformant of the Present Invention and Reduction Reaction Example (part 2)

(1) Provision for Preparing Gene Having Base Sequence Coding Amino Acid Sequence of Protein Having Ability of Converting Oxidized β-nicotinamide Adenine Dinucleotide into Reduced Type

*Bacillus megaterium* IFO12108 strain was cultured in 100 ml of sterilized LB medium, to obtain 0.4 g of cell. From this cell, chromosome DNA (hereinafter, referred to as chromosome DNA (C)) was purified using Qiagen Genomic Tip (manufactured by Qiagen) according to a method described in the appended manual.

(2) Preparation of Gene Having Base Sequence Coding Amino Acid Sequence of Protein Having Ability of Converting Oxidized β-nicotinamide Adenine Dinucleotide into Reduced Type Based on a sequence of glucose dehydrogenase derived from *Bacillus megaterium* IWG3 described in The Journal of Biological Chemistry Vol. 264, No. 11, 6381-6385 (1989), an oligonucleotide primer having a base sequence shown in SEQ ID NO:12 and an oligonucleotide primer having a base sequence shown in SEQ ID NO:13 were synthesized.

Using the oligonucleotide primer having a base sequence shown in SEQ ID NO:12 and the oligonucleotide primer having a base sequence shown in SEQ ID NO:13 as a primer, PCR was carried out under the following reaction solution composition and reaction condition using the above-mentioned chromosome DNA (C) as a template (using Expand High Fidelity PCR System, manufactured by Roche Diagnostics).

[Reaction Solution Composition]

| | |
|---|---|
| chromosome DNA stock solution | 1 μl |
| dNTP (each 2.5 mM-mix) | 0.4 μl |
| primer (20 pmol/μl) | each 0.75 μl |
| 10× buffer (with MgCl) | 5 μl |
| enz.expand HiFi (3.5 × $10^3$ U/ml) | 0.375 μl |
| ultrapure water | 41.725 μl |

[PCR Reaction Condition]

A vessel containing a reaction solution of the above-mentioned composition was set on PERKIN ELMER-GeneAmp PCR System 2400, and heated at 97° C. (2 minutes), then, a cycle of 97° C. (0.25 minutes)-55° C. (0.5 minutes)-72° C. (1.5 minutes) was repeated 10 times, then, a cycle of 97° C. (0.25 minutes)-55° C. (0.5 minutes)-72° C. (2.5 minutes) was repeated 20 times, further, the reaction solution was kept at 72° C. for 7 minutes.

Thereafter, a part of the PCR reaction solution was collected and subjected to agarose gel electrophoresis, to detect a band of a DNA fragment of about 950 bp.

The DNA fragment of about 950 bp obtained by PCR was ligated to the existence "PCR Product insertion site" of pCR2.1-TOPO vector using the resulting PCR reaction solution and using TOPO™TA cloning kit Ver. E manufactured by Invitrogen, and in the resulting ligation liquid, E. coli DH5α was transformed.

On a LB agar medium containing 50 μg/ml ampicillin, 30 μl of X-gal 4% aqueous solution and 30 μl of 0.1 M IPTG were applied, and the resulting transformant was inoculated to this and cultured. One white colony among the formed colonies was collected, and this colony was inoculated to sterilized LB medium (2 ml) containing 50 μg/ml ampicillin, and cultured in a test tube while shaking (30° C., 24 hours). From the cultured cell, a plasmid was taken out using QIAprep Spin Miniprep Kit (manufactured by Qiagen). A part of the taken out plasmid was digested with a restriction enzyme (EcoRl), then, subjected to electrophoresis, to confirmed that the DNA fragment of about 950 bp was inserted into the plasmid (hereinafter, this plasmid is referred to as pSDGDH12).

The base sequence of the DNA fragment inserted into pSDGDH12 was analyzed. The result is shown in SEQ ID NO:14.

For analysis of the base sequence of the DNA fragment inserted into the plasmid, a sequence reaction was carried out using plasmid pSDGDH12 as a template, using Dye Terminator Cycle sequencing FS ready Reaction Kit (manufactured by Perkin Elmer) and the base sequence of the resulting DNA was analyzed by DNA sequencer 373A (manufactured by Perkin Elmer).

Next, based on the base sequence shown in SEQ ID NO:14, oligonucleotide primers having base sequences shown in SEQ ID NO:15 and SEQ ID NO:16 were synthesized.

Using the oligonucleotide primers having base sequences shown in SEQ ID NO:15 and SEQ ID NO:16, PCR was carried out under the following reaction solution composition and reaction condition using the above-mentioned chromosome DNA (C) as a template (using Expand High Fidelity PCR System, manufactured by Roche Diagnostics).

[Reaction Solution Composition]

| | |
|---|---|
| chromosome DNA stock solution | 1 μl |
| dNTP (each 2.5 mM-mix) | 0.4 μl |
| primer (20 pmol/μl) | each 0.75 μl |
| 10× buffer (with MgCl) | 5 μl |
| enz. expand HiFi (3.5 × $10^3$ U/ml) | 0.375 μl |
| ultrapure water | 41.725 μl |

[PCR Reaction Condition]

A vessel containing a reaction solution of the above-mentioned composition was set on PERKIN ELMER-GeneAmp PCR System 2400, and heated at 97° C. (2 minutes), then, a cycle of 97° C. (0.25 minutes)-55°C. (0.5 minutes)-72° C. (1.5 minutes) was repeated 10 times, then, a cycle of 97° C. (0.25 minutes)-55° C. (0.5 minutes)-72° C. (2.5 minutes) was repeated 20 times, further, the reaction solution was kept at 72° C. for 7 minutes.

Thereafter, a part of the PCR reaction solution was collected and subjected to agarose gel electrophoresis, to detect a band of a DNA fragment of about 800 bp.

To the remaining PCR reaction liquid was added 2 kinds of restriction enzymes (Ncol and BamHl), and the DNA fragment of about 800 bp was double-digested, then, the enzymaticaly digested DNA fragment was purified.

On the other hand, plasmid vector pTrc99A (manufactured by Pharmacia) was double-digested with 2 kinds of restriction enzymes (Ncol and BamHl), and the enzymaticaly digested DNA fragment was purified.

These enzymaticaly digested DNA fragments were mixed, and ligated with T4 DNA ligase, and E. coli DH5α was transformed with the resulting ligation liquid.

The resulting transformant was cultured on a LB agar medium containing 50 μg/ml ampicillin, and from grown colonies, 10 colonies were selected randomly. These selected colonies were inoculated to sterilized LB media (2 ml) each containing 50 μg/ml ampicillin, and cultured in a test tube while shaking (37° C., 17 hours). From the cultured cells, plasmids were taken out using QIAprep Spin Miniprep Kit (manufactured by Qiagen). Respective parts of the taken out plasmids were double-digested with 2 kinds of restriction enzymes of Ncol and BamHl, then, subjected to electrophoresis, and it was confirmed that the above-mentioned DNA fragment of about 800 bp was inserted into 4 plasmids among the taken out plasmids (hereinafter, this plasmid is referred to as plasmid pTrcGDH).

(3) Preparation of Vector of the Present Invention

Using the oligonucleotide primer having a base sequence shown in SEQ ID NO:17 and the oligonucleotide primer having a base sequence shown in SEQ ID NO:11 as a primer, PCR was carried out under the following reaction solution composition and reaction condition using plasmid pTrcRYF as a template (using Expand High Fidelity PLUS PCR System, manufactured by Roche Diagnostics).

[Reaction Solution Composition]

| | |
|---|---|
| cDNA library stock solution | 1 μl |
| dNTP (each 2.5 mM-mix) | 4 μl |
| primer (50 pmol/μl) | each 0.4 μl |
| 5× buffer (with MgCl) | 10 μl |

| | |
|---|---|
| Expand High Fidelity PLUS Taq polymerase | 0.5 μl (2.5 U) |
| ultrapure water | 33.7 μl |

[Reaction Condition]

A vessel containing a reaction solution of the above-mentioned composition was set on PERKIN ELMER-GeneAmp PCR System 9700, and heated at 94° C. (2 minutes), then, a cycle of 94° C. (0.25 minutes)-55° C. (0.5 minutes)-72° C. (1.5 minutes) was repeated 10 times, then, a cycle of 94° C. (0.25 minutes)×55° C. (0.5 minutes)-72° C. (1.0 minute+5 seconds/cycle) was repeated 20 times, further, the reaction solution was kept at 72° C. for 7 minutes.

Thereafter, a part of the PCR reaction solution was collected and subjected to agarose gel electrophoresis, to detect a band of a DNA fragment of about 1000 bp.

To the remaining PCR reaction liquid was added 2 kinds of restriction enzymes (BamHl and Xbal), and the DNA fragment of about 1000 bp was double-digested, then, the enzymaticaly digested DNA fragment was purified.

On the other hand, plasmid pTrcGDH was double-digested with 2 kinds of restriction enzymes (BamHl and Xbal), and the enzymaticaly digested DNA fragment was purified.

These enzymaticaly digested DNA fragments were ligated with T4 DNA ligase, and E. coli DH5α was transformed with the resulting ligation liquid. The resulting transformant was cultured on a LB agar medium containing 50 μg/ml ampicillin, and from grown colonies, 6 colonies were selected randomly. These selected colonies were inoculated to sterilized LB media (2 ml) each containing 50 μg/ml ampicillin, and cultured in a test tube while shaking (30° C., 17 hours). From the cultured cells, plasmids were taken out using QIAprep Spin Miniprep Kit (manufactured by Qiagen). Respective parts of the taken out plasmids were double-digested with 2 kinds of restriction enzymes of BamHl and Xbal, then, subjected to electrophoresis, and it was confirmed that the intended DNA fragment of about 1000 bp was inserted into all of the taken out plasmids (hereinafter, this plasmid is referred to as plasmid pTrcGSRYF).

(4) Preparation of Transformant of the Present Invention and Reduction Reaction Example Using plasmid pTrcGSRYF, E. coli HB101 was transformed. The resulting transformant was inoculated to sterilized LB medium (100 ml) containing 0.1 mM IPTG and 50 μg/ml ampicillin, and cultured while shaking (30° C., 17 hours). The resulting culture medium was centrifugally separated to obtain 0.49 g of a wet cell.

3.0 g of ethyl 2-oxo-4-phenylbutyrate, 0.49 g of the above-mentioned wet cell, 3.0 mg of NAD$^+$, 4.5 g of glucose and 30 ml of 100 mM phosphate buffering solution (pH 7.0) were mixed and stirred at 30° C. for 27 hours. During stirring, 2M sodium carbonate aqueous solution was added gradually so that the reaction solution had a pH of 7.0. Thereafter, to the reaction liquid was added 50 ml of ethyl acetate, then, centrifugal separation was performed to obtain an organic layer. This organic layer was dehydrated over magnesium sulfate, and ethyl acetate was distilled off, to obtain 2.4 g of ethyl 2-hydroxy-4-phenylbutyrate. The optical purity of the resulting ethyl 2-hydroxy-4-phenylbutyrate was measured, to find 98.5% e.e. for (R) configuration.

(Content Analysis Condition)

Column: DB-1 (0.53 mm×30 m, 1.5 μm) (manufactured by J&W Scientific)

Column temperature: 50° C. (0 minute)→4° C./minute→170° C. (0 minute)→30° C./minute→290° C. (4 minutes)

Carrier gas: helium (column flow rate: 10 ml/minute)

Detector: FID (Optical Purity Measuring Condition)

Column: Chirasil-Dex-CB (0.32 mm×25 m, 0.25 μm) (manufactured by CHROMPACK)

Column temperature: 100° C. (0 minute)→2° C./minute→180° C. (0 minute)

Carrier gas: helium (column flow rate: 1.5 ml/minute)

Detector: FID

Slit ratio: 1/50

The absolute configuration of the product was determined by comparison with a standard sample of ethyl (R)-2-hydroxy-4-phenylbutyrate.

Example 4

Reduction Reaction Example of Transformant of the Present Invention (part 2)

Using plasmid pTrcGSRYF, E. coli HB101 was transformed. The resulting transformant was inoculated to sterilized LB medium (100 ml) containing 0.1 mM IPTG and 50 μg/ml ampicillin, and cultured while shaking (30° C., 17 hours). The resulting culture medium was centrifugally separated to obtain 0.49 g of a wet cell.

3.0 g of ethyl 2-oxo-4-phenylbutyrate, 0.49 g of the above-mentioned wet cell, 3.0 mg of NAD$^+$, 4.5 g of glucose, 30 ml of 100 mM phosphate buffering solution (pH 7.0) and 6 ml of butyl acetate were mixed and stirred at 30° C. for 9 hours. During stirring, 2M sodium carbonate aqueous solution was added gradually so that the reaction solution had a pH of 7.0. Thereafter, to the reaction liquid was added 50 ml of ethyl acetate, then, centrifugal separation was performed to obtain an organic layer. This organic layer was dehydrated over magnesium sulfate, and ethyl acetate was distilled off, to obtain 3.0 g of ethyl 2-hydroxy-4-phenylbutyrate. The optical purity of the resulting ethyl 2-hydroxy-4-phenylbutyrate was measured, to find 100% e.e. for (R) configuration.

(Content Analysis Condition)

Column: DB-1 (0.53 mm×30 m, 1.5 μm) (manufactured by J&W Scientific)

Column temperature: 50° C. (0 minute)→4° C./minute→170° C. (0 minute)→30° C./minute→290° C. (4 minutes)

Carrier gas: helium (column flow rate: 10 ml/minute)

Detector: FID (Optical Purity Measuring Condition)

Column: Chirasil-Dex-CB (0.32 mm→25 m, 0.25 μm) (manufactured by ASTECH)

Column temperature: 100° C. (0 minute)→2° C./minute→180° C. (0 minute)

Carrier gas: helium (pressure 55 Kpa)

Detector: FID

Slit ratio: 1/50

The absolute configuration of the product was determined by comparison with a standard sample of ethyl (R)-2-hydroxy-4-phenylbutyrate.

What is claimed is:

1. An isolated nucleic acid molecule comprising a nucleotide sequence selected from the group consisting of:
   a) a nucleotide sequence coding the amino acid sequence of SEQ ID NO:1,
   b) a nucleotide sequence which has a sequence homology of at least 95% with a nucleotide sequence coding the amino acid sequence of SEQ ID NO:1, and which encodes a protein having the ability to asymmetrically reduce ethyl 2-oxo-4-phenylbutyrate to produce ethyl (R)-2-hydroxy-4-phenylbutyrate,
   c) a nucleotide sequence which hybridizes under a stringent condition to a DNA molecule having a nucleotide sequence coding the amino acid sequence of SEQ ID NO:1, and which encodes a protein having the ability to asymmetrically reduce ethyl 2-oxo-4-phenylbutyrate to produce ethyl (R)-2-hydroxy-4-phenylbutyrate, wherein the stringent condition comprises a washing step at 65° C. for 30 minutes in 0.1×SSC, and
   d) the nucleotide sequence of SEQ ID NO:2.

2. An isolated nucleic acid molecule obtained by connecting a promoter functional in a host cell with the nucleic acid molecule according to claim 1 in a functional form.

3. A recombinant vector comprising the nucleic acid molecule according to claim 1.

4. A recombinant vector comprising the nucleic acid molecule according to claim 2.

5. A transformant obtained by introducing the nucleic acid molecule according to claim 2 into the host cell.

6. The transformant according to claim 5, wherein the host cell is a microorganism.

7. The transformant according to claim 5, wherein the host cell is E. coli.

8. A transformant obtained by introducing the recombinant vector according to claim 3 into a host cell.

9. The transformant according to claim 8, wherein the host cell is a microorganism.

10. The transformant according to claim 8, wherein the host cell is E. coli.

11. A transformant comprising the nucleic acid molecule according to claim 1.

12. A method of producing a transformant, comprising a process of introducing the recombinant vector according to claim 3 into a host cell.

13. A method of producing a transformant, comprising a process of introducing the recombinant vector according to claim 4 into the host cell.

14. A recombinant vector comprising the nucleic acid molecule according to claim 1 and a nucleic acid molecule comprising a nucleotide sequence coding a protein having the ability to convert oxidized β-nicotinamide adenine dinucleotide or oxidized β-nicotinamide adenine dinucleotide phosphoric acid into a reduced type.

15. The recombinant vector according to claim 14, wherein the protein having the ability to convert oxidized β-nicotinamide adenine dinucleotide or oxidized β-nicotinamide adenine dinucleotide phosphoric acid into a reduced type is a glucose dehydrogenase.

16. A transformant obtained by introducing the recombinant vector according to claim 14 into a host cell.

17. The transformant according to claim 16, wherein the host cell is a microorganism.

18. The transformant according to claim 16, wherein the host cell is E. coli.

19. A transformant obtained by introducing the recombinant vector according to claim 15 into a host cell.

20. The transformant according to claim 19, wherein the host cell is a microorganism.

21. The transformant according to claim 19, wherein the host cell is E. coli.

22. A transformant comprising the nucleic acid molecule according to claim 1 and a nucleic acid molecule comprising a nucleotide sequence coding a protein having the ability to convert oxidized β-nicotinamide adenine dinucleotide or oxidized β-nicotinamide adenine dinucleotide phosphoric acid into a reduced type.

23. A method of producing an (R)-2-hydroxy-4-phenylbutyrate, comprising allowing the transformant according to claim 16 or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

24. A method of producing an (R)-2-hydroxy-4-phenylbutyrate, comprising allowing the transformant according to claim 17 or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

25. A method of producing an (R)-2-hydroxy-4-phenylbutyrate, comprising allowing the transformant according to claim 18 or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

26. A method of producing an (R)-2-hydroxy-4-phenylbutyrate, comprising allowing the transformant according to claim 19 or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

27. A method of producing an (R)-2-hydroxy-4-phenylbutyrate, comprising allowing the transformant according to claim 20, or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

28. A method of producing an (R)-2-hydroxy-4-phenylbutyrate, comprising allowing the transformant according to claim 21 or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

29. A method of producing an (R)-2-hydroxy-4-phenylbutyrate, comprising allowing the transformant according to claim 22 or a treated product of the transformant to act on a 2-oxo-4-phenylbutyrate, wherein the treated product of the transformant is selected from the group consisting of a lyophilized transformant, an organic solvent-treated transformant, a dried transformant, a disrupted transformant, an autolysate of the transformant, an ultrasonic-treated transformant, an extraction product of the transformant, and an alkali-treated transformant.

30. An isolated nucleic acid molecule comprising a nucleotide sequence that encodes a polypeptide having at least 95% amino acid sequence identity to SEQ ID NO:1, wherein the polypeptide has the ability to asymmetrically reduce ethyl 2-oxo-4-phenylbutyrate to produce ethyl (R)-2-hydroxy-4-phenylbutyrate.

31. A recombinant vector comprising the nucleic acid molecule of claim 30.

32. A transformant comprising the nucleic acid molecule of claim 30.

33. A method of producing a polypeptide having at least 95% amino acid sequence identity to SEQ ID NO:1, wherein the polypeptide has the ability to asymmetrically reduce ethyl 2-oxo-4-phenylbutyrate to produce ethyl (R)-2-hydroxy-4-phenylbutyrate, the method comprising
  allowing the transformant of claim 32 express the polypeptide; and
  obtaining the polypeptide from the transformant.

* * * * *